United States Patent
Simpson et al.

(10) Patent No.: US 7,583,368 B1
(45) Date of Patent: Sep. 1, 2009

(54) METHOD OF ENHANCING MEASUREMENT OF STRESS IN GLASS

(75) Inventors: Jeffrey A. Simpson, Wayne, NE (US); Mark A. Imbrock, Sylvania, OH (US); Nathan Strimpel, Carleton, MI (US)

(73) Assignee: Electronic Design To Market, Inc., Toledo, OH (US)

( * ) Notice: Subject to any disclaimer, the term of this patent is extended or adjusted under 35 U.S.C. 154(b) by 381 days.

(21) Appl. No.: 11/731,739

(22) Filed: Mar. 30, 2007

Related U.S. Application Data

(60) Provisional application No. 60/789,838, filed on Apr. 5, 2006.

(51) Int. Cl.
*G01L 1/24* (2006.01)
*G01B 9/02* (2006.01)

(52) U.S. Cl. .................. 356/35.5; 356/491; 73/800

(58) Field of Classification Search ............... 356/35.5, 356/491, 496, 495, 484; 73/800, 802
See application file for complete search history.

(56) References Cited

U.S. PATENT DOCUMENTS

| | | | |
|---|---|---|---|
| 1,503,543 A | 8/1924 | Lytle | |
| 1,756,785 A | 4/1930 | Gallasch | |
| 3,016,464 A | 1/1962 | Bailey | |
| 3,137,756 A | 6/1964 | Günther et al. | |
| 3,693,025 A | 9/1972 | Brunton | |
| 3,807,870 A | 4/1974 | Kalman | |
| 3,994,586 A | 11/1976 | Sharkins et al. | |
| 4,207,467 A | 6/1980 | Doyle | |
| 4,284,356 A | 8/1981 | Heilman | |
| 4,353,649 A * | 10/1982 | Kishii | 356/33 |
| 4,655,589 A * | 4/1987 | Cestaro et al. | 356/35 |
| 4,848,913 A | 7/1989 | Greiner | |
| 4,899,055 A | 2/1990 | Adams | |
| 4,902,902 A | 2/1990 | Tole | |
| 4,984,894 A | 1/1991 | Kondo | |
| 5,054,927 A | 10/1991 | Garves | |
| 5,132,631 A | 7/1992 | Klopfenstein et al. | |
| 5,237,392 A | 8/1993 | Hickel et al. | |
| 5,239,488 A | 8/1993 | Markham et al. | |
| 5,254,149 A | 10/1993 | Hashemi et al. | |
| 5,341,204 A * | 8/1994 | Grant et al. | 356/35.5 |
| 5,442,573 A | 8/1995 | Bredberg et al. | |
| 5,490,728 A | 2/1996 | Schietinger et al. | |
| 5,525,138 A | 6/1996 | Hashemi et al. | |
| 5,564,830 A | 10/1996 | Bobel et al. | |
| 5,568,264 A | 10/1996 | Nakatsuka et al. | |

(Continued)

FOREIGN PATENT DOCUMENTS

CA 2539676 A1 9/2006

(Continued)

*Primary Examiner*—Patrick J Connolly
(74) *Attorney, Agent, or Firm*—MacMillan, Sobanski & Todd, LLC

(57) ABSTRACT

A detection system for measuring glass that has been placed under strain and the resulting stress lines in the glass has a light source of individual elements configured to create a light distribution. The light distribution has a discontinuity which enhances the viewing of a photoelastic effect in the glass. The light source creates a viewable optical interference (i.e., color changes) which results from stress lines in the glass.

31 Claims, 4 Drawing Sheets
(1 of 4 Drawing Sheet(s) Filed in Color)

U.S. PATENT DOCUMENTS

| | | |
|---|---|---|
| 5,581,355 A | 12/1996 | Myers et al. |
| 5,597,237 A | 1/1997 | Stein |
| 5,637,873 A | 6/1997 | Davis et al. |
| 5,657,124 A | 8/1997 | Zhang et al. |
| 5,726,749 A | 3/1998 | Schave |
| 5,726,756 A | 3/1998 | Aki et al. |
| 5,727,017 A | 3/1998 | Maurer et al. |
| 5,748,091 A | 5/1998 | Kim |
| 5,838,446 A | 11/1998 | Meth et al. |
| 5,966,214 A | 10/1999 | Imbrock et al. |
| 6,175,416 B1 * | 1/2001 | Maris et al. .................. 356/630 |
| 6,683,695 B1 | 1/2004 | Simpson et al. |
| 7,061,612 B2 | 6/2006 | Johnston |
| 7,268,860 B1 * | 9/2007 | Chen .......................... 356/35.5 |
| 2006/0054843 A1 | 3/2006 | Simpson et al. |
| 2006/0209304 A1 | 9/2006 | Simpson et al. |

FOREIGN PATENT DOCUMENTS

| | | |
|---|---|---|
| DE | 22584 | 1/1962 |
| EP | 0480027 A | 4/1992 |
| GB | 2321309 B | 8/1999 |
| JP | 53-16652 A | 2/1978 |
| JP | 56-44804 A | 4/1981 |
| JP | 60-147606 A | 8/1985 |
| SU | 1585670 A | 8/1990 |
| WO | WO 99/58928 A1 | 11/1999 |
| WO | WO 01/07882 A1 | 2/2001 |

\* cited by examiner

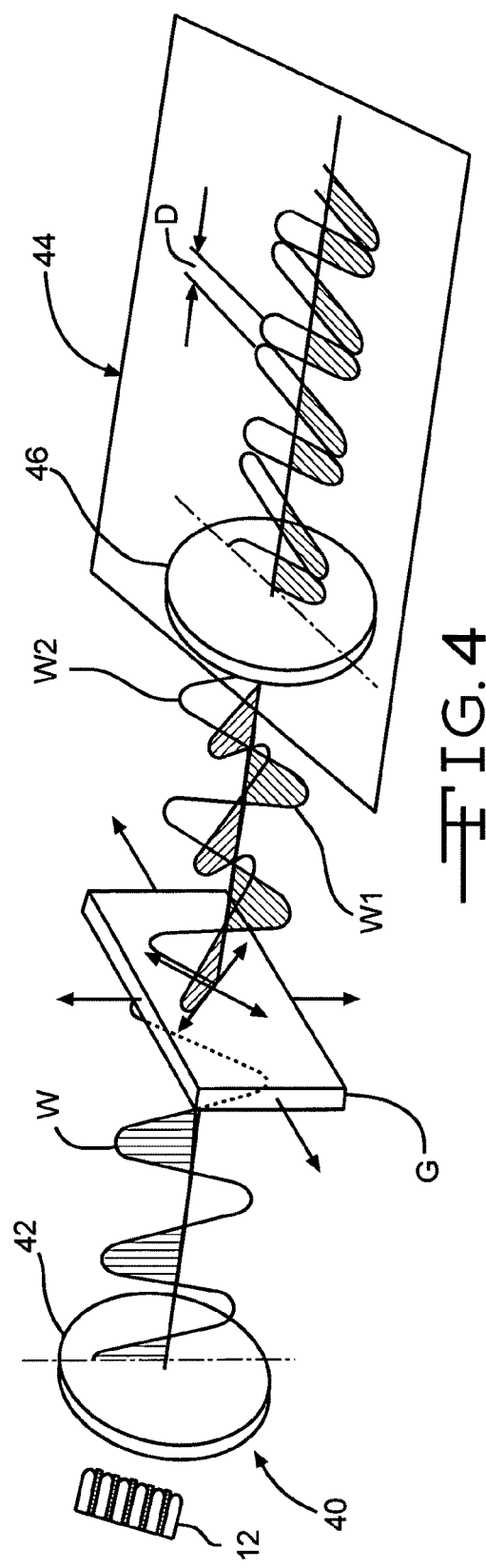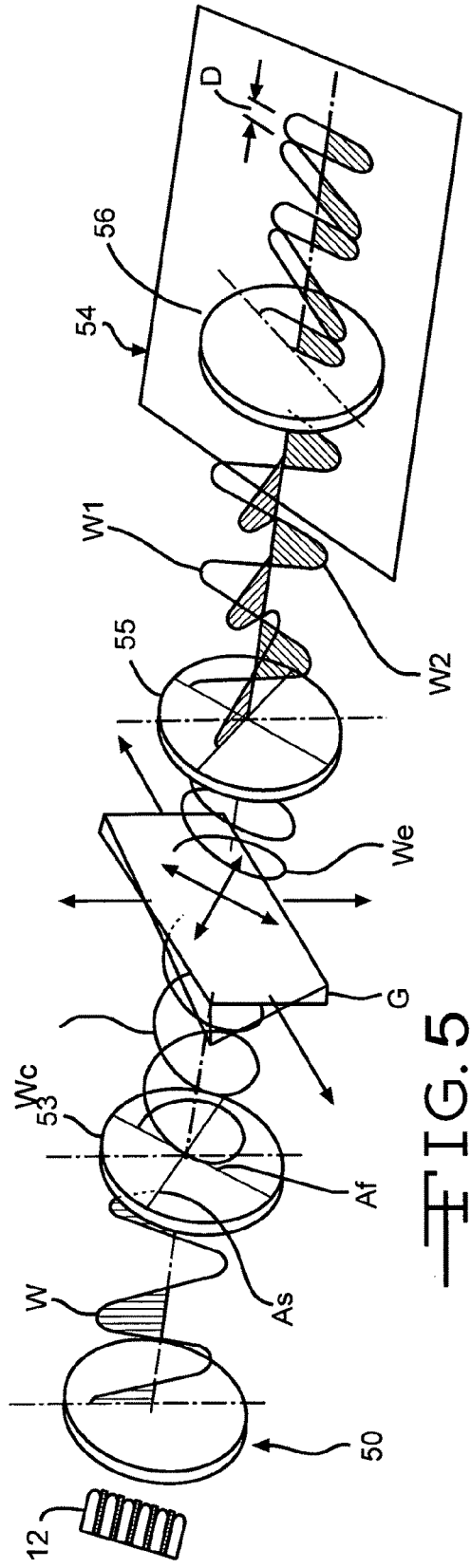

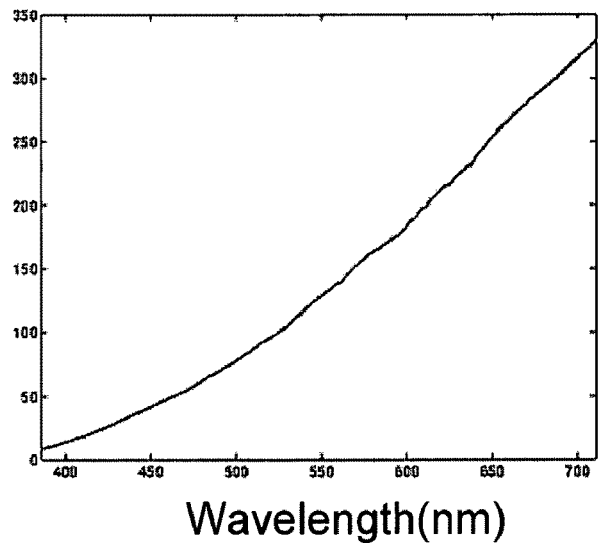

Tungsten Lamp Spectrum

FIGURE 6

| Color | Relative Retardation | Equivalent Fringe Order for monochromatic Light | |
|---|---|---|---|
| | Nanometer (10-9 m) | Mercury Green 546.1 nm | Sodium 489.3 nm |
| First Order Colors | | | |
| Black | 0 | 0.00 | 0.00 |
| Grey | 140 | 0.29 | 0.27 |
| White | 260 | 0.48 | 0.44 |
| Pale Yellow | 330 | 0.64 | 0.59 |
| Orange | 460 | 0.84 | 0.78 |
| Dull Red | 520 | 0.95 | 0.88 |
| Purple | 580 | 1.06 | 0.98 |
| Deep Blue | 620 | 1.14 | 1.05 |
| Blue-Green | 700 | 1.28 | 1.19 |
| Second Order Colors | | | |
| Green-Yellow | 830 | 1.46 | 1.36 |
| Orange | 960 | 1.72 | 1.59 |
| Rose Red | 1050 | 1.90 | 1.78 |
| Purple | 1150 | 2.10 | 1.95 |
| Green | 1350 | 2.50 | 2.30 |
| Third Order Colors | | | |
| Green-Yellow | 1450 | 2.65 | 2.45 |
| Pink | 1550 | 2.85 | 2.60 |
| Green | 1800 | 3.30 | 3.05 |
| Fourth Order Colors | | | |
| Pink | 2100 | 3.85 | 3.55 |
| Green | 2400 | 4.40 | 4.05 |

FIGURE 7

METHOD OF ENHANCING MEASUREMENT OF STRESS IN GLASS

CROSS-REFERENCE TO RELATED APPLICATION

The present invention claims the benefit of the provisional patent application Ser. No. 60/789,838 filed Apr. 5, 2006.

BACKGROUND OF THE INVENTION

In order to produce a safer pane of glass, the commercial and residential window industry has developed strengthened glass. The strengthened glass shatters into small pieces where non-strengthened (regular) glass breaks into sharp pieces that can cause serious injury. Current legal codes and regulations require strengthened glass to be used in certain applications. Manufacturers of windows need to confirm they have strengthened glass for to meet quality control requirements. Window installers need to verify the correct window is being used in order to pass inspections. Likewise, inspectors need to verify that the strengthened glass in various installations meets city, state and federal regulations.

The standard method used by industry to determine whether glass meets stress/strengthening requirements is to use a polarimeter. For example, one previous method uses a broadband light source using a line filament lamp, as shown in Prior Art FIG. 1. The line filament lamp L imitates the broad light spectrum for the visible light region. The continuous light output C by the lamp passes through a polarizer P and is reflected back from each surface of a glass G being tested. The reflected light passes back through the same polarizer P. Since the continuous light is reflected back at an angle, the user has to turn or hold his head at a sharp angle with respect to the meter in order to take a reading. This is inconvenient for the user and can cause inaccurate readings. Another current product requires the user to run the meter across the glass pane in search of any color change that may occur. This color change is not always obvious or easy to detect. With this product, the user also must turn or hold his head at an angle with respect to the glass being tested. The holding one's head at the correct angle needed, while performing the test, can be difficult and in tight spaces, practically impossible.

The current products also require a rechargeable battery because there is a huge power draw by the line filament light source which has broadband wavelength output. The filament type light source causes the battery to die out quickly and the user must recharge it frequently. This can be a huge inconvenience when testing multiple panes of glass.

There is a demand for a faster and more convenient method of detecting the presence of "stress" lines within strengthened glass. Also, there is a demand for a detection system that has longer battery life.

BRIEF SUMMARY OF THE INVENTION

In one aspect, there is provided a detection system for examining glass that has been placed under strain and detecting any resulting stress lines in the glass. The detection system includes a light source that creates a discontinuous light distribution emitted to and reflected from the glass. The light distribution has a discontinuity which enhances the viewing of a photoelastic effect in the glass.

In certain embodiments, the light source can be a line of individual elements. In a particular embodiment, the individual elements can have a limited visible light spectrum. In other embodiments, the light source can be a pulsating light source. The light source can be comprised of one or more elements that do not contain a filament, such as, for example, LED's.

Also, the light source can have an unequal power distribution of light to detect stress lines in the glass. In such embodiments, the unequal power distribution can be across a line of light created from multiple, spaced-apart light sources.

The light source also creates a viewable optical interference that results from stress lines in the glass. The viewable optical interference can comprise color changes.

Also, in another aspect, the light source comprises a limited spectrum light source in alignment with a polarizer. The polarizer rotates reflected light to detect the presence of stress lines in the glass. In one embodiment, the polarizer includes one or more linear polarizers configured to maximize an isoclinic pattern for electronic detection of the stress lines. In another embodiment, the polarizer includes a circular polarizer configured to maximize an isochromatic pattern for manual detection of the stress lines. In such embodiment, the light source can comprise individual elements having a limited visible light spectrum such that the isochromatic pattern is not monochromatic or does not contain all of the wavelengths of the visible light spectrum.

In another aspect, the detection system can further include a prism or other optical device to align the reflected light with a sensor that is configured to detect the presence of stress lines within the glass. The prism or other optical device is configured to create lines or indicators that are spaced apart.

In another aspect, there is provided a method measuring strain and/or stress lines in glass. A light source having a limited spectrum is aligned with a polarizer. The light source creates a light distribution which enhances a viewing of a photoelastic effect in the glass and creates a viewable optical interference resulting from stress lines in the glass. The limited spectrum light is reflected from the glass, and any strain present in the glass is detected.

The method can include using a line or array of light which is discontinuous in order to detect the presence of stress lines in strengthened glass. The discontinuity of light occurs at a desired spacing. The method can also include using a light source comprised of individual elements in a line, and correlating the light reflections from the light source to allow measurement of glass thickness.

Also, in certain methods, an unequal power distribution of light is used to detect stress lines in strengthened glass. The unequal power distribution is across a line of light created from multiple light sources.

In certain methods, discrete light sources are in alignment with the polarizer. Also, mechanical or manual means of light rotation can be used to detect the presence of stress lines in strengthened glass. A circular polarizer can be used to maximize an isochromatic pattern for manual or electronic detection with the light source. Alternatively, linear polarizers can be to maximize an isoclinic pattern for electronic detection.

In still other methods, a prism is aligned with the light source to detect the presence of stress lines within glass.

Various objects and advantages of this invention will become apparent to those skilled in the art from the following detailed description of the preferred embodiment, when read in light of the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Prior Art FIG. 1 schematically illustrates a line filament light glass stress meter.

FIG. 4 is a schematic illustration of a plane polarizer useful in a LED glass stress/strain detection system.

FIG. 5 is a schematic illustration of a circular polarizer useful in a LED glass stress/strain detection system.

FIG. 6 is a graph showing the wavelength of a tungsten lamp spectrum.

FIG. 7 is a table showing color produced by a progressive increase of stress on glass.

DETAILED DESCRIPTION OF THE INVENTION

In one aspect, there is provided a detection system 10 for measuring a glass G that has been placed under strain and any resulting stress lines in the glass.

Figure 1:
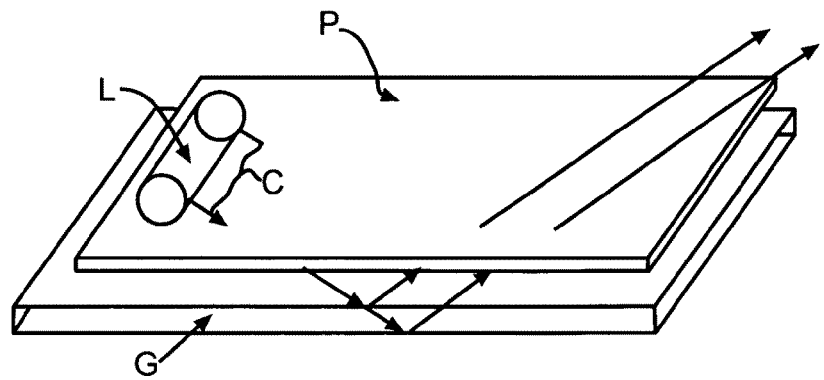
Figure 2:
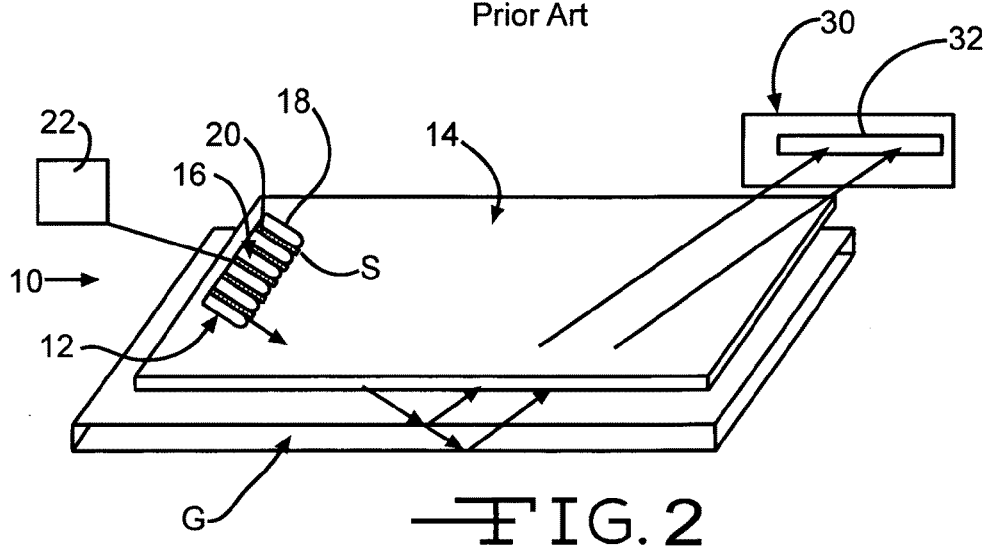
FIG. 2 schematically illustrates one embodiment of a LED glass stress/strain detection system.

In the embodiment shown in FIG. 2, the detection system 10 includes a light source 12 that is in alignment with a polarizer 14. The polarizer 14 can be any suitable device for rotating reflected light to detect the presence of stress lines in the glass.

The detection system 10 includes a light source 12 that creates a discontinuous light distribution. The discontinuous light distribution has a discontinuity that enhances the viewing of any photoelastic effect in the glass. The light source 12 is also configured to create a viewable optical interference resulting from stress lines in the glass G. In certain embodiments, the viewable optical interference comprises visible color changes.

In a particular embodiment, the light source 12 is a limited spectrum light source which is different from a monochrome or broadband light source (i.e., sun or a filament type lamp), which is commonly referred to as white light.

The detection system 10 creates and utilizes a discontinuous line of light in order to intensify the user's perception of any change in the strengthened glass G. In the embodiment shown herein, the limited spectrum light source 12 comprises a line or an array 16 where the limited spectrum light is generated from one or more discrete (i.e., separate or individual) light emanating elements 18.

In certain embodiments, the light source 12, comprised of individual limited spectrum light emanating elements 18, creates a distribution of discrete light reflections. The discontinuity in reflected light, in turn, enhances the viewing of a photoelastic effect in the glass. The light source 12 also creates a viewable optical interference (i.e., color changes) which results from stress lines in the glass.

In one particular embodiment, the individual limited spectrum light emanating elements 18 are light emitting diodes, or LED's. In general, LED's have generally round light-emitting end shape. It is first to be noted that while the reflection of visible filament-type lamp from a glass is about 4%, the light emanating from an LED is significantly smaller than a filament type lamp. Also, to be noted is that the limited spectrum light from the round end shape of the LED causes a reduction or diffusion of the light being emitted therefrom.

The limited spectrum light source 12 has a light output that generally follows a Gaussian curve in which the center of output is more intense than its edges. When the light source is an LED, the Gaussian or rounded shape of the output curve causes a problem when trying to locate a reflection of a LED-generated light off a specific surface of glass. The round LED reflection from each glass surface may be too large and the adjacent reflections tend to blend into each other, making it difficult to differentiate between reflections.

The present invention provides a solution by using a limited spectrum light source 12 that includes the non-continuous line or array 16 of discrete, or separate, limited spectrum light elements 18.

In certain embodiments, the visual perspective is further increased by having a plurality of LED light source elements 18 used in the array 16. The LED light source elements 18 are placed next to each other to produce a longer line, or array, 16. In this embodiment, the array 16 of light has the same discontinuity and uneven power distribution no matter how closely the LED light source elements 18 are spaced since the LEDs are, in fact, individual light sources. Thus, it is within the contemplated scope of the embodiments described herein that the discontinuity of light can occur at a desired spacing that can be of equidistance or can be of varied distances.

It is also within the contemplated scope that in certain embodiments, the light source 12 can provide a non-uniform light spectrum in conjunction with the non-continuous light source to detect the presence of a strengthened glass.

In the embodiment shown herein, the limited spectrum light elements 18 comprising the array 16 are separated by using a non-light transmitting material 20 to block portions of the LED output. The non-light transmitting material 20 is configured to achieve a desired shape of light being directed to (and thus reflected from) the glass surface.

The non-light transmitting material 20 modifies the amount and direction of light emanating from the limited spectrum light elements 18. In one embodiment, the non-light transmitting material 20 comprises a plurality of light-blocking walls that are parallel to each other and positioned on opposite sides each of the light source elements 18. Each non-light transmitting material 20 has a desired width that such that there a gap, or discontinuity, in the light being transmitted to the glass G. The gap that is present between the adjacent light-blocking walls 20 determines a final thickness of each generated line of light emanating from the array 17 of limited spectrum light elements 18.

The separate light source elements 18 of the light source 12 thus create spaces S between glass surface reflections. An unequal power distribution is created across the line, or area, of light which, in turn, amplifies the eye's visual perspective of the light color change. This provides a distinct advantage when the light source elements are LED's since the LED light spectrum is not continuous over the entire visible light spectrum.

The LED light source elements 18 are positioned at a specific angle with respect to the glass G so that the space S between reflections is optimized. This angle allows easy viewing of each surface reflection. The space S between each reflection may be correlated to a thickness measurement of the glass.

Thus, the discontinuity of light occurs at a desired spacing. Also, each light source element 18 has an unequal power distribution of light that is then used to detect stress lines in the glass. The unequal power distribution is across a line of light that is created from the multiple, and spaced-apart, light source elements 18. In certain embodiments, the light source elements 18 can be pulsating light sources. Also, in certain embodiments, it is desired that the light source 12 does not contain a filament-type light.

In certain embodiments, the detection system 10 is powered by a battery 22. The use of LED light sources 12 reduces the current draw on the battery 22. Also, the LED light source 12 may be flashed on and off at a rate greater than that viewed by the human eye. This flashing of the LED light source 12 yields a light that is perceived to be always on, but requires less draw on the battery 22 than a constantly lit LED light source 12.

In certain embodiments, an optical lens arrangement 30 may be used to focus the reflections from a second glass surface reflection onto a sensor 32 in order to distinguish between different thicknesses of glass. Any change in the reflected light caused by the stress lines in the glass G is detected by the sensor 32 and is analyzed to again create a GO-NO GO sensor. If the reflection is focused on the sensor 32 that is a colored charge coupled device (CCD) or other light sensor, the amount of stress can be quantified, using for example, the data shown in the table in FIG. 7.

FIG. 6 shows the common spectrum of a 60-watt tungsten light bulb used by industry. Since the eye is more perceptible to color change, rather than a change in intensity (energy) at a certain color (wavelength), the color changing effect is used in the present inventive detection system 10 to provide a highly accurate and sensitive detection system.

The color change is directly related to the amount of stress located on the stress line. The table in FIG. 7 illustrates the color of stress produced by a progressive increase of stress in the glass. If the light source has a limited light spectrum, the specific color as defined in the table may not be available in the source light. Therefore, it would not show up in the end results.

Figure 8:
FIG. 8 is a photograph of individual LED lights source reflections on tempered glass.
Figure 9:
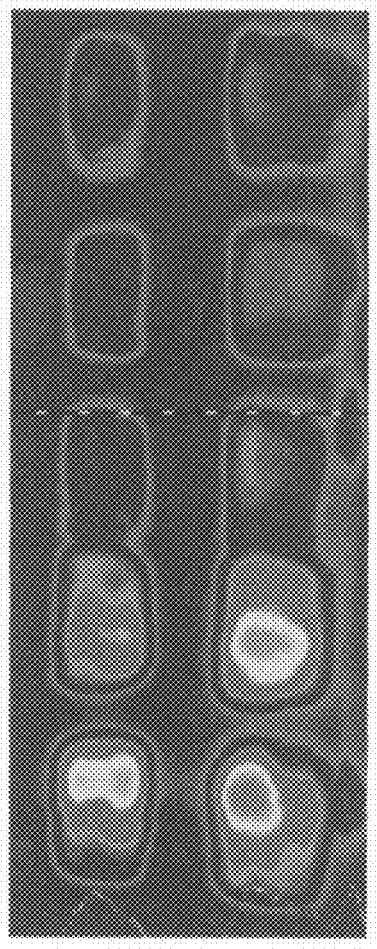
FIG. 9 is a photograph of individual LED lights source reflections on clear glass.

FIG. 8 illustrates the colors from a limited spectrum, non-continuous light source array on tempered (strengthened) glass using a camera. FIG. 9 illustrates the colors from a limited spectrum, non-continuous light source array on clear glass using a camera. The Surface 2 of LED light sources represents the reflected light signal from the second surface of glass. This reflected light has traveled through and back across the strengthened glass.

In certain embodiments, the polarizer 16 of the detection system 10 is a linear polarimeter 40, as schematically illustrated in FIG. 4. The linear polarizer 40 is used to maximize an isoclinic pattern for electronic detection. Light is applied to the linear polarizer 42 and the exiting light W is polarized to its optical axis. When the glass G is in a state of strain, the glass G possesses the property of splitting each ray of light that passes through the glass G into separate components. The polarized light is therefore split into perpendicular waves $W_1$ and $W_2$ of different amplitude and phases, depending on the amount of strain on the glass. These two waves $W_1$ and $W_2$ are then passed through an analyzer 44 that can include another polarizer 46 that recombines the two waves $W_1$ and $W_2$. The recombined waves vibrate in the same plane, but retain a phase difference D. Since the waves $W_1$ and $W_2$ are now in the same plane this causes an optical interference which, in turn, produces the possibility of colors. Lighter and darker spots will be created from a monochromatic light source. A white light source will produce results of color change as well as dark shading.

Under certain conditions, however, the resulting dark shading may overpower the color change. It has been further discovered that using a circular polarimeter 50, as schematically illustrated in FIG. 5, eliminates the dark spots that may overshadow the color change. The circular polarimeter 50 maximizes an isochromatic pattern for the detection of light.

As shown in FIG. 5, light L is applied to a first polarizer 52 and the exiting light W is polarized to its optical axis. The light W is passed through a first quarter wave plate 53 that has a fast axis $a_f$ and a slow axis $a_s$ such that the light $W_c$ is circularly polarized.

When the glass G is in a state of strain, the glass G possesses the property of splitting each ray of light that passes through the glass G into separate components. The polarized light is therefore split into elliptically polarized light $W_e$ which is then passed through a second quarter wave plate 55 that also has a fast axis and a slow axis. The elliptically polarized light $W_e$ passes through the second quarter wave plate 55 as perpendicular waves $W_1$ and $W_2$ of different amplitude and phases, depending on the amount of strain on the glass. These two waves $W_1$ and $W_2$ then are passed through an analyzer 54 that can include a second polarizer 56 that recombines the two waves $W_1$ and $W_2$. The recombined waves vibrate in the same plane, but retain a phase difference D. Since the waves $W_1$ and $W_2$ are now in the same plane this causes an optical interference which, in turn, produces the possibility of colors.

Since the light source 12 comprises individual elements, each having a limited visible light spectrum, the isochromatic pattern is not monochromatic or does not contain all of the wavelengths of the visible light spectrum.

Figure 3:
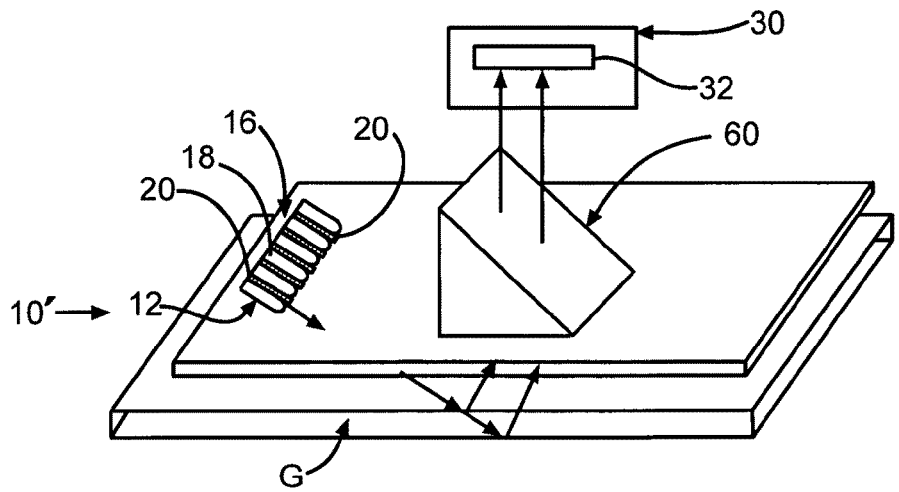
FIG. 3 schematically illustrates another embodiment of a LED glass stress/strain detection system.

Referring now to FIG. 3, another embodiment of a detection system 10' is schematically illustrated. It is to be noted that, for the same or similar structures as shown in FIG. 2, the same reference numbers will be used for ease of explanation. In the embodiment in FIG. 3, the detection system 10' further includes a prism 60 or other optical device in alignment with the light source 12 to aid in detecting the presence of stress lines within the glass. The prism 60 is used in the detection system to angle the reflected light for easy viewing by the user, as shown in FIG. 3. A scale (not shown) may be added to measure the distance between the glass surfaces to ultimately determine the thickness of the glass pane.

The prism 60 allows the user to view the strain lines in a direct manner instead of viewing the strain lines at an angle. This embodiment allows the user to rotate the detection system 10' in a plane parallel to the glass surface. The use of the prism 60 enhances the change in light since the angle at which the light interacts with the stress line is directly related to the perceived color change. The detection system 10' provides a significant improvement over the prior types or units which had to be slid around on the glass surface and which required viewing the reflections at an awkward angle instead of head on.

The angle of the light in reference to the stress line is related to the colors observed. To optimize the angle in reference to the stress lines, the light source can be rotated until the optimal angle is observed (i.e., greatest color change is observed). This can be achieved by rotating the detection system mechanically or manually. A similar effect can be obtained by rotating the glass against the sensor, however, since the majority of the windows are large and sometimes attached, this process is often impossible.

In another aspect, the present invention relates to a method of improving the detection of glass which has been placed under strain and the resulting stress lines within the glass. The method includes the use of a non-uniform limited light spectrum source in correlation with a polarizer to detect the presence of glass which is in a state of strain or has been strengthened.

It is to be understood that various suitable algorithms or mathematical techniques can be used with the present invention. Further, the detection system may be controlled and/or operated by conventional control and/or operational systems, including, but not limited to various software instructions and/or programs. It is to be understood that such instructions and programs are readily available to, or readily programmable, without undue experimentation from the descriptions as provided herein.

The patent or application file contains at least one drawing executed in color. Copies of this patent with color drawing(s) will be provided by the United States Patent and Trademark Office upon request and payment of necessary fee While the invention has been described with reference to a preferred embodiment, it should be understood by those skilled in the art that various changes may be made and equivalents may be substituted for elements thereof without departing from the essential scope of the invention. In addition, many modifications may be made to adapt a particular situation to the teachings of the invention without departing from the essential scope thereof. Therefore, it is intended that the invention not be limited to the particular embodiment disclosed as the best mode contemplated for carrying out this invention, but that the invention will include all embodiments falling within the scope of the claims.

What is claimed is:

1. A detection system for measuring glass that has been placed under strain and any resulting stress lines in the glass, comprising: at least one light source configured to create a non-continuous light distribution; the light distribution being configured to have a discontinuity which enhances the viewing of a photoelastic effect in the glass, wherein the light source is configured to create a viewable optical interference resulting from stress lines in the glass.

2. The detection system of claim 1, wherein the viewable optical interference comprises visible color changes.

3. The detection system of claim 1, wherein the light source comprises at least one limited spectrum light source in alignment with at least one polarizer.

4. The detection system of claim 1, further including a device for rotating reflected light.

5. The detection system of claim 4, wherein the rotating device is mechanical or manual.

6. The detection system of claim 1, wherein the discontinuity of light occurs at a desired spacing.

7. The detection system of claim 1, wherein the light source has an unequal power distribution of light.

8. The detection system of claim 7, wherein the unequal power distribution is across a line of light created from multiple, spaced-apart light source elements.

9. The detection system of claim 1, wherein the light source comprises at least one pulsating light source.

10. The detection system of claim 1, wherein the light source does not contain a filament-type light.

11. The detection system of claim 1, wherein the light source comprises an array of individual light source elements.

12. The detection system of claim 11, wherein one or more of the individual elements have a limited visible light spectrum.

13. The detection system of claim 1, wherein the light source is configured to allow measurement of thickness of the glass.

14. The detection system of claim 1, further including at least one circular polarizer configured to maximize an isochromatic pattern for detection of any stress lines in the glass, wherein the isochromatic pattern is not monochromatic or so limited in wavelength to be considered a single color neither does the pattern contain all of the wavelengths of the visible light spectrum.

15. The detection system of claim 14, wherein the light source comprises individual elements having a limited visible light spectrum.

16. The detection system of claim 1, furthering including one or more linear polarizers configured to maximize an isoclinic pattern for detection of any stress lines in the glass.

17. The detection system of claim 1, further including at least one prism or other optical device configured to create lines or indicators that are spaced apart.

18. The detection system of claim 1, further including at least one prism or other optical device configured to align light from the glass with at least one sensor that is configured to detect the presence of stress lines within the glass.

19. The detection system of claim 1, wherein i) the light source comprises at least one limited spectrum light source in alignment with at least one polarizer, wherein the light source has an unequal power distribution of light to detect stress lines in the glass, and wherein the unequal power distribution is across a line of light created from multiple, spaced-apart light source elements; and, ii) the detection system further includes at least one prism configured to align light reflected from the glass with at least one sensor that is configured to detect the presence of stress lines within the glass.

20. A method for measuring stain or stress lines in glass, comprising: providing a light source, creating a discontinuous distribution of light from the light source, generating a viewable optical interference which results from any stress lines present in the glass, and detecting any strain present in the glass.

21. The method of claim 20, wherein in the light source has a limited spectrum.

22. The method of claim 20, wherein the discontinuity of light occurs at a desired spacing.

23. The method of claim 20, including using an unequal power distribution of light to detect stress lines in the glass.

24. The method of claim 23, wherein the unequal power distribution is across a line of light created from multiple light source elements.

25. The method of claim 20, including using a pulsating light source.

26. The method of claim 20, wherein the light source does not contain a filament-type light.

27. The method of claim 20, further including correlating reflections from the light source to allow measurement of glass thickness.

28. The method of claim 20, further including rotating the light to detect the presence of stress lines in strengthened glass.

29. The method of claim 28, wherein the rotating of the light includes using at least one circular polarizer to maximize an isochromatic pattern for detection of any stress lines in the glass.

30. The method of claim 28, wherein the rotating of the light includes using at least one linear polarizer to maximize an isoclinic pattern for detection of any stress lines in the glass.

31. The method of claim 20, including aligning at least one prism with the light source.

* * * * *